United States Patent [19]

Phillips et al.

[11] 4,033,346
[45] July 5, 1977

[54] ADJUSTMENT DEVICE FOR DRENCH GUNS OR SYRINGES

[75] Inventors: Ian Ross Phillips, Pymble; Mervyn Frank Reynolds, Dee Why, both of Australia

[73] Assignee: N. J. Phillips Pty. Limited, Dee Why, Australia

[22] Filed: Aug. 9, 1976

[21] Appl. No.: 712,976

[30] Foreign Application Priority Data

Aug. 21, 1975  Australia .................... 2874/75

[52] U.S. Cl. .................... 128/223; 128/234
[51] Int. Cl.² .................................. A61D 7/00
[58] Field of Search .......... 128/223, 224, 234, 235, 128/218 C, 218 G

[56] References Cited

UNITED STATES PATENTS

| | | | |
|---|---|---|---|
| 1,982,993 | 12/1934 | Kauzal | 128/223 |
| 2,074,401 | 3/1937 | Kauzal | 128/223 |
| 3,682,175 | 8/1972 | Halter | 128/223 |

FOREIGN PATENTS OR APPLICATIONS

| | | | |
|---|---|---|---|
| 104,220 | 6/1938 | Australia | 128/223 |
| 102,184 | 10/1937 | Australia | 128/223 |

*Primary Examiner*—John D. Yasko
*Attorney, Agent, or Firm*—Ladas, Parry, Von Gehr, Goldsmith & Deschamps

[57] ABSTRACT

A liquid dispensing gun employing an interacting bore, piston and piston rod which gun is provided with adjustment means to determine the volume of liquid delivered by the gun. The adjustment means being a series of projections extending radially from the peripheral surface of the piston rod and arranged thereon to selectively engage a circular member located around the rod, which circular member is provided with a series of recesses extending longitudinally adjacent the rod into which the projections may enter.

12 Claims, 6 Drawing Figures

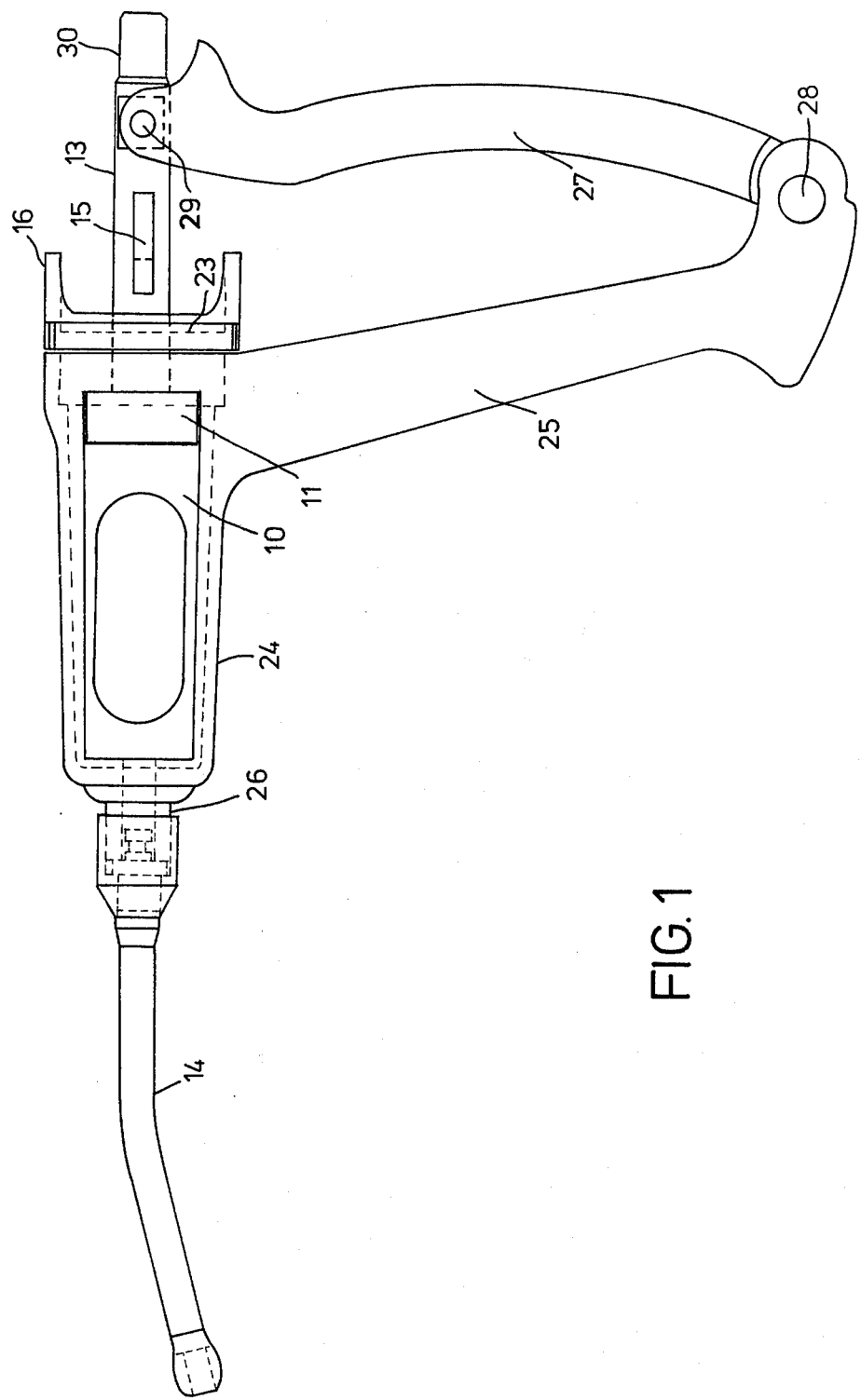

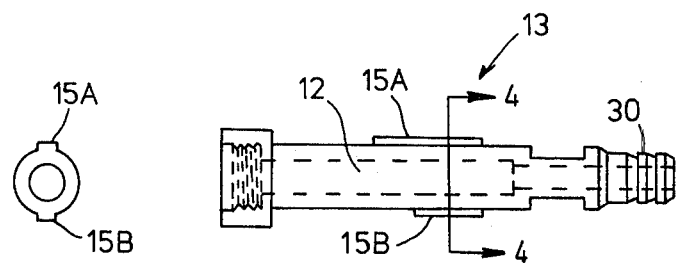
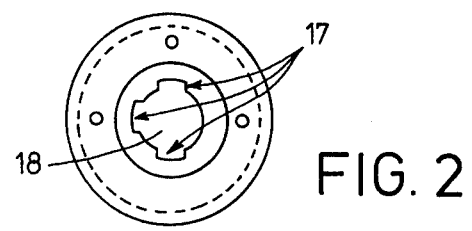
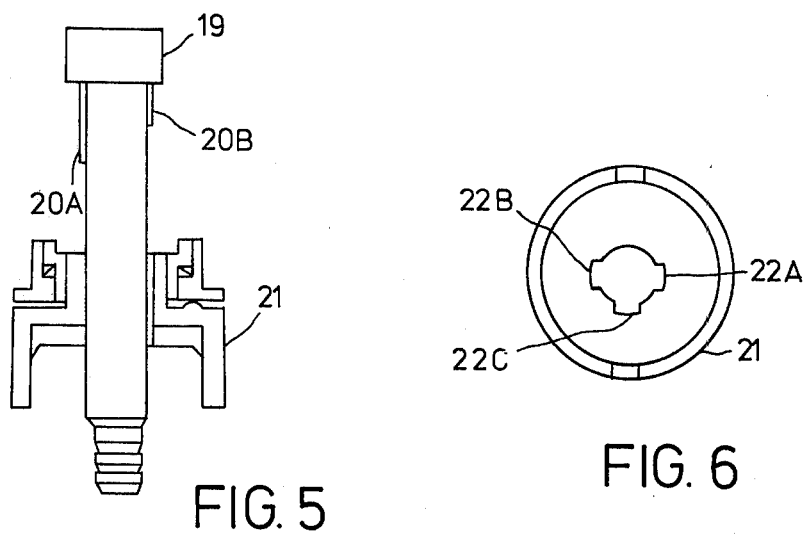

ADJUSTMENT DEVICE FOR DRENCH GUNS OR SYRINGES

This invention relates to drench guns or syringes for the dosing of animals, especially sheep and cattle, and more particularly the present invention is an improvement in adjustable dosage guns or syringes.

It is desirable in drench guns that means be provided to enable the volume of dosage delivered into an animal be predetermined, thus in the past some drench guns have been provided with adjustment means which means is usually in the form of a threaded stop member engageable within a threaded passage. The other end of the stop member engages a lug or portion of the trigger to thereby limit its travel. Such adjustment mechanisms are usually located at the lower junction of the trigger and handle as depicted in Applicant's copending application Ser. No. 678,578.

In certain circumstances a continuous adjustment such as that described above is not required and more especially is inconvenient, time consuming and inaccurate. An example of such a circumstance is when the dosage delivered has to be changed frequently and only a limited number of different volumes is required.

It is the object of the present invention to provide a drench gun ameliorating the above disadvantages by providing an adjustment mechanism having a limited number of selectable positions which determine the dosage delivered by the gun.

Accordingly in a first form the present invention provides a drench gun having an interacting bore and piston, a piston rod extending from said piston, and adjustment means to limit the travel of said piston and piston rod to thereby determine either the dosage delivered by or drawn into the gun, said adjustment means comprising a projection extending radially from the peripheral surface of said rod, recessed means rotatable about and located adjacent said rod, a recess in said recessed means extending longitudinally adjacent said rod and dimensioned and positionable to allow said projection to enter into or pass therethrough whereby said projection when not aligned with said recess limits the travel of the rod in one direction by engagement with said recessed means while when aligned said projection is allowed to travel further in said direction by entering said recess.

In a second form the present invention provides a drench gun having an interacting bore and piston, a piston rod extending from said piston, and adjustment means to limit the travel of said piston and piston rod to thereby determine the dosage delivered by or drawn into said gun, said adjustment means comprising at least two projections extending radially from the peripheral surface of and spaced at different longitudinal positions along said rod, recessed means rotatable about and located adjacent said rod, at least two recesses in said recessed means extending longitudinally adjacent said rod, said projections and recesses being angularly spaced around said rod so that when simultaneously each of the projections aligns with a recess said piston is allowed to travel its maximum distance in one direction by said projections entering or passing through said recesses, and whereupon rotation of said recessed means through a predetermined angle cause at least one projection to become misaligned to thereby limit the travel of said piston in said direction.

It should be realised that the present invention is not limited to the use of one or two projections as the adjustment means may be formed to accommodate any number of projections. However, the recesses in the adjustment means preferably should be equally spaced except for the space between one pair of adjacent recesses which is twice that of any other space. The projections are similarly spaced. Also the projections should be at different longitudinal positions along the rod so that a different volume of dose is associated with each projection.

A preferred form of the present invention will now be described by way of example with reference to the accompanying drawings wherein:

FIG. 1 is an elevation depicting a drench gun partly sectioned.

FIG. 2 is the rotatable adjustment means of FIG. 1.

FIG. 3 is the piston rod of FIG. 1.

FIG. 4 is the cross-section 4—4 of the piston rod of FIG. 3.

FIG. 5 is an arrangement for limiting the return stroke of the piston of FIG. 1.

FIG. 6 is the rotatable adjustment member of FIG. 5.

The drench gun of FIG. 1 has a cylindrical central chamber 10 within whih slides piston 11 to either draw in a fresh dose via the duct 12 in the piston rod 13 (see FIG. 3) or to force the dose out through the nozzle 14. The dosage delivered in this particular case is adjusted in volume by limiting the injecting stroke of the piston. This is done by means of the splines 15 located on the piston rod 13 and the rotatable adjustment member 16 located around piston rod 13. The rotatable member 16 (see FIG. 2) is provided with slots 17 and a central passage 18 through which the piston rod 13 slides. The rotatable member 16 is rotatable about the axis of and relative to the piston rod 13 so that either one or both of the splines 15, is allowed to pass through or enter the slots 17. As the splines 15 extend different lengths in the direction of the rotatable member 16 the piston rod 13 is allowed to move a distance according to which one of the splines 15 engages a face 23 of the rotatable member 16. If both the splines are in alignment with a slot 17 then neither engage and thus the piston will travel its maximum distance into chamber 10.

With the piston rod 13 having two splines 15 and the rotatable member 16 having three slots 17 (A, B and C) any one of three different dosage volumes may be selected and injected. Firstly, as illustrated the piston rod 13 would have maximum travel as the splines 15 line up with two of the slots 17, secondly if the rotatable member 16 is rotated 90° in either direction then one of the two splines 15 will engage the rotatable member 16 to thus limit the travel of the piston rod 13. As the splines 15 are of different lengths the volumes associated with the engagement of either spline is different.

If the piston rod 13 of FIG. 3 was provided with a further spline then there would be four different dosage volumes, one corresponding to 0°, 90°, 180° and 270° rotation of the rotatable member 16. If the number of slots 17 was increased along with the number of splines 15 a still further number of dosage volumes would be available.

In the gun described with reference to FIGS. 1 to 4 the volume injected is determined by the injecting stroke of the piston while the following description relates to a similar gun but the volume of dose injected is regulated by the backward stroke of the piston, that is the gun's intake of dose is adjusted.

Referring now to FIGS. 5 and 6 wherein the rightward movement of piston 19 may be limited by the splines 20 (A and B) engaging the rotatable member 21, with slots 22 (A, B and C).

In the embodiment depicted in FIGS. 1 to 4 the body portion 24 of the gun is provided with raised portion 31 which engage recesses 32 in the rotatable member to define the adjustment positions of the gun, each adjustment portion providing a different volume of dose. The embodiment of FIGS. 5 and 6 is similarly provided with means to define the adjustment portions.

The gun illustrated in FIG. 1 is of conventional construction, except for the adjustment means, by being provided with a body portion 24 within which is formed the cylinder 10. Theb body portion 24 is moulded integrally with the handle 25 and is provided with threaded means 26 to which is attached nozzle 14. The trigger 27 is pivotally attached to the lower portion of the handle 25 by pin 28 and attached to piston rod 13 by trunion 29.

The piston 11 may sealingly engage the walls of the cylinder 10 by known suitable means such as an "O" ring or resilient cup located on the leading face of the piston.

It is conventional for the trigger 27 and the handle 25 to be biased apart by a leaf spring of "V" shape located therebetween. Thus after an injecting stroke the trigger 27 returns to the depicted position and simultaneously draws a fresh dose into the gun through a supply conduit attached to end 30 of rod 13.

What we claim is:

1. A drench gun having an interacting bore and piston, a piston rod extending from said piston, and adjustment means to limit the travel of said piston and piston rod to thereby determine either the dosage delivered by or drawn into the gun, said adjustment means comprising a projection extending radially from the peripheral surface of said rod, recessed means rotatable about and located adjacent said rod, a recess in said recessed means extending longitudinally adjacent said rod and dimensioned and positionable to allow said projection to enter into or pass therethrough, whereby said projection when not aligned with said recess limits the travel of the rod in one direction by engagement with said recessed means while when aligned said projection is allowed to travel further in said direction by entering said recess.

2. A drench gun having an interacting bore and piston, a piston rod extending from said piston, and adjustment means to limit the travel of said piston and piston rod to thereby determine the dosage delivered by or drawn into said gun, said adjustment means comprising at least two projections extending radially from the peripheral surface of and spaced at different longitudinal positions along said rod, recessed means rotatable about and located adjacent said rod, at least two recesses in said recessed means extending longitudinally adjacent said rod, said projections and recesses being angularly spaced around said rod so that when simultaneously each of the projections aligns with a recess said piston is allowed to travel its maximum distance in one direction by said projections entering or passing through said recesses, and whereupon rotation of said recesses means through a predetermined angle cause at least one projection to become misaligned to thereby limit the travel of said piston in said direction.

3. A drench gun according to claim 2 wherein the projections are located remote from the piston, and the adjustment means limits the movement of the piston into the bore.

4. A drench gun according to claim 3, wherein there are two projections and three recesses, said projections being located 180° apart, and two of said recesses being 180° apart, while the third recess is located intermediate the other two recesses thereby providing the gun with three adjustment positions.

5. A drench gun according to claim 2 wherein there are three projections and three recesses, the three projections and also the three recesses being located 90°, 90° and 180° apart respectively thereby providing the gun with four adjustment positions.

6. A drench gun according to claim 2 wherein there are four projections and four recesses, said projection and said recesses being spaced at 72° intervals around said rod except for two projections and two recesses which are spaced apart by 144° to thereby provide the gun with five adjustment positions.

7. A drench gun according to claim 2 wherein means are provided to define the angular positions of the recessed means which correspond to adjustment positions.

8. A drench gun having an interacting bore and piston, a piston rod extending from said piston, and adjustment means to limit the travel of said piston and piston rod to thereby determine the dosage delivered by or drawn into said gun, said adjustment means comprising at least two projections extending radially from the peripheral surface of and spaced at different longitudinal positions along the end portion of the rod adjacent the piston, recessed means rotatable about and located adjacent said rod, at least two recesses in said recessed means extending longitudinally adjacent said rod, said projections and recesses being angularly spaced around said rod so that when simultaneously each of the projections aligns with a recess said piston rod is allowed to travel its maximum distance out of said bore by said projections entering or passing through said recesses, and whereupon rotation of said recessed means through a predetermined angle to cause at least one projection to become misaligned to thereby limit the travel of said piston in said direction.

9. A drench gun according to claim 8 wherein there are two projections and three recesses, said projections being located 180° apart, and two of said recesses being 180° apart, while the third recess is located intermediate the other two recesses thereby providing the gun with three adjustment positions.

10. A drench gun according to claim 8 wherein there are three projections and three recesses, the three projections and also the three recesses being located 90°, 90° and 180° apart respectively thereby providing the gun with four adjustment positions.

11. A drench gun according to claim 8 wherein there are four projections and four recesses, said projection and said recesses being spaced at 72° intervals around said rod except for two projections and two recesses which are spaced apart by 144° to thereby provide the gun with five adjustment positions.

12. A drench gun according to claim 11 wherein means are provided to define the angular positions of the recessed means which correspond to adjustment positions.

* * * * *